United States Patent
Strong

[11] Patent Number: 5,840,091
[45] Date of Patent: Nov. 24, 1998

[54] SMOG AND DUST FILTER FOR A TRACHEOSTOMY TUBE

[75] Inventor: Samuel E. Strong, Toledo, Ohio

[73] Assignee: Steve Culpepper, Bowling Green, Ohio

[21] Appl. No.: 871,868

[22] Filed: Jun. 9, 1997

Related U.S. Application Data

[63] Continuation of Ser. No. 501,803, Jul. 13, 1995, abandoned.

[51] Int. Cl.$^6$ .................................................. B01D 46/00
[52] U.S. Cl. .......................... 55/385.1; 55/487; 55/505; 55/507; 55/DIG. 35; 128/207.14
[58] Field of Search .................................. 55/385.1, 486, 55/487, 488, 489, 504, 505, 507, DIG. 35; 95/273, 286, 287; 128/207.14, 207.15, 207.16, 207.19

[56] References Cited

U.S. PATENT DOCUMENTS

| | | | |
|---|---|---|---|
| 865,189 | 9/1907 | Lamb | 55/505 |
| 1,734,125 | 11/1929 | Greene | 55/488 |
| 1,883,715 | 10/1932 | Greene | 55/487 |
| 2,008,560 | 7/1935 | Nutting | 55/489 |
| 2,039,142 | 4/1936 | Brehm | 128/207.17 |
| 2,205,599 | 6/1940 | Mitchell | 55/505 |
| 2,491,647 | 12/1949 | Colavita | 128/207.14 |
| 2,521,094 | 9/1950 | Rein | 55/505 |
| 3,101,709 | 8/1963 | Gruenewaelder | 128/206.12 |
| 3,330,271 | 7/1967 | Hozier | 128/205.29 |
| 3,464,410 | 9/1969 | Buchanan | 128/205.29 |
| 3,548,823 | 12/1970 | Bogacik | 55/DIG. 35 |
| 3,811,436 | 5/1974 | Ferrell | 128/205.29 |
| 3,905,788 | 9/1975 | Alliger | 55/489 |
| 4,083,706 | 4/1978 | Wiley | 55/385.1 |
| 4,090,513 | 5/1978 | Togawa | 55/DIG. 35 |
| 4,325,366 | 4/1982 | Tabor | 128/207.16 |
| 4,360,018 | 11/1982 | Choski | 55/DIG. 35 |
| 4,463,757 | 8/1984 | Schmidt | 128/205.29 |
| 4,763,645 | 8/1988 | Kapp | 128/205.29 |
| 4,971,054 | 11/1990 | Andersson et al. | 128/207.16 |
| 5,042,468 | 8/1991 | Lambert | 128/200.26 |
| 5,147,430 | 9/1992 | Kidd | 55/505 |
| 5,201,309 | 4/1993 | Friberg et al. | 128/207.14 |
| 5,259,378 | 11/1993 | HUchon et al. | 128/207.16 |
| 5,294,236 | 3/1994 | Baird | 55/505 |
| 5,468,383 | 11/1995 | McKenzie | 55/507 |
| 5,487,382 | 1/1996 | Bezicot | 128/207.14 |

Primary Examiner—Duane S. Smith
Attorney, Agent, or Firm—Marshall & Melhorn

[57] ABSTRACT

A smog and dust filter for a tracheostomy tube which easily adapts onto existing tracheostomy tubes to filter out dust and airborne contaminants. The light weight and unobtrusive filter is easily manufactured and quickly installed onto an existing tracheostomy tube. The filter includes a securing device for engaging the outer periphery of an open end of a tracheostomy tube. A filter element, having two or more layers of net material, is attached to the securing device. The layers provide a filtering membrane to separate airborne particles and contaminants from an inhaled air stream.

6 Claims, 1 Drawing Sheet

5,840,091

SMOG AND DUST FILTER FOR A TRACHEOSTOMY TUBE

This application is a continuation, of application No. 08/501,803, filed Jul. 13, 1995, now abandoned.

BACKGROUND OF THE INVENTION

1. Field of the Invention

This invention relates to a filter apparatus for a tracheostomy tube. More particularly, this invention relates to a filter made from a synthetic net material that covers the open end of a tracheostomy tube to prevent dust and airborne particles from entering the lungs of the individual using the tracheostomy tube.

2. Summary of Related Art

Tracheostomy tubes are utilized with patients who have a permanently damaged or obstructed airway. The tracheostomy tube creates an unobstructed airway to permit normal breathing. However, the tube bypasses the natural filters of the nasal cavities in the normal airway. Therefore, ambient air inhaled through the tracheostomy tube travels directly to the lungs without being filtered.

In the prior art, tracheostomy tube filters are generally complex filtration devices that require extensive fabrication. The known filtration devices are therefore costly and not readily available to all users of tracheostomy tubes. Additionally, some of the devices require special tracheostomy tubes or adaptors in order to hold the filter. The filtration devices in the prior art do not provide a filter which is easily fitted over the end of an existing tracheostomy tube to prevent the inhalation of airborne contaminants.

U.S. Pat. No. 4,763,645 discloses a filtering device which covers the outer end of a tracheostomy tube. The filter housing is either fitted into or snap fitted over the outer end of the tracheostomy tube. The filtration is provided by a coarse screen and a disposable filter element. The filter element is contained within the filter housing and is attached to a threaded, removable end cap. The threaded end cap attaches to corresponding threads on the filter housing. The patent discloses the use of various plastics, metals, or metal alloys for use in fabricating the filter housing and the threaded end cap.

U.S. Pat. No. 5,042,468 discloses a breathing device which serves as a filter element attached to the open end of a tracheostomy tube. The apparatus also includes a heat moisture exchanger for conditioning inhaled air. A holder is inserted into the outer end of the tracheostomy tube. The heat moisture exchanger, having a flat filter body, is then attached by flanges to the holder.

U.S. Pat. No. 3,464,410 discloses a respiratory pad utilized in filtering and conditioning inhaled air. The patent claims the use of a respiratory pad over a neck opening resulting from a tracheostomy. The pad comprises several layers of fibrous material through which inhaled air passes.

It would be an advantage to have a filter for a tracheostomy tube that easily fits over the end of an existing tracheostomy tube to filter dust and other airborne particles.

It would also be an advantage to have a tracheostomy tube filter with an uncomplicated design that does not require extensive fabrication and is produced at a low cost.

SUMMARY OF THE INVENTION

In accordance with the present invention, there is provided a smog and dust filter for a tracheostomy tube. The filter easily adapts onto existing tracheostomy tubes to filter out dust and airborne contaminants. The light weight and unobtrusive filter is easily manufactured and quickly installed onto an existing tracheostomy tube.

The filter of the present invention comprises a securing means for engaging an outer periphery of an open end of a tracheostomy tube while the tube is inserted into an individual.

A filter element, having two or more layers of net material, is attached to the securing means. The layers of net material create a filtering section on the filter element. The layers of net material are randomly aligned to create a micro porous membrane within the filter section. As the securing means is placed over the tracheostomy tube, the filtering section covers the open end of the tracheostomy tube. The micro porous membrane separates dust and airborne contaminants from the air stream upon inhalation by the individual.

It is an object of the present invention to provide a filter for a tracheostomy tube that easily fits over the open end of an existing tracheostomy tube. The present invention provides a filtering device that securely attaches to the open end of the tracheostomy tube without difficulty in order to filter airborne contaminants from the inhaled air stream..

A further object of the present invention is to provide a filter for a tracheostomy tube that is easily manufactured at a relatively low production cost. The uncomplicated design of the present invention does not require extensive molding or fabrication as seen in the prior art.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

DESCRIPTION OF THE PREFERRED EMBODIMENT

Figure 1:
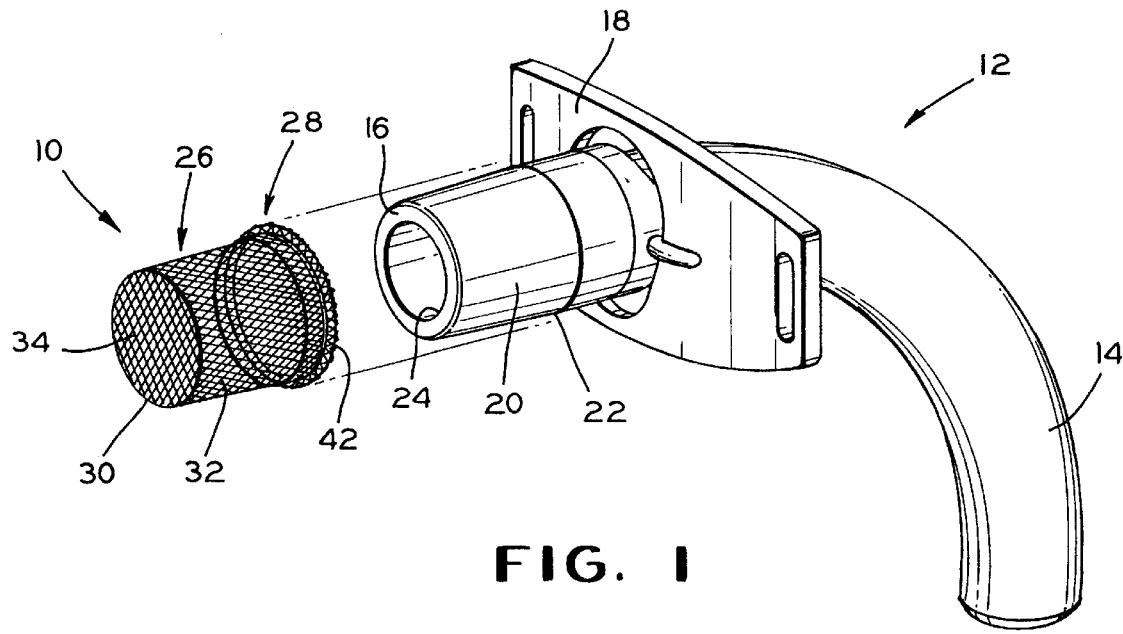
FIG. 1 is a perspective view of a tracheostomy tube with the present invention positioned for placement over the open end of the tracheostomy tube.

Referring now more particularly to the drawings, there is illustrated generally in FIG. 1 the tracheostomy tube filter 10 of the present invention. The device 10 is placed onto a tracheostomy tube 12 to filter dust and airborne contaminants upon inhalation by the individual using the tracheostomy tube.

The present invention is designed for use with a tracheostomy tube 12 as indicated in FIG. 1. The tracheostomy tube forms no part of the present invention. The tracheostomy tube 12 serves as the apparatus upon which the present invention is utilized. The tracheostomy tube has an insertion end 14, and open end 16, and a pivotal collar 18. The open end 16 has an end cap 20 with an outer periphery 22 that tapers toward an opening 24 in the open end 16. The pivotal collar 18 protects from over insertion of the tube and maintains the appropriate positioning of the tube 12 while inserted into an individual. The tracheostomy tube 12 depicted in FIG. 1 is used for illustrative purposes. The present invention may be used on other tracheostomy tubes configured differently than the one depicted, but all of which have an open end upon which the present invention may be placed.

The filter 10 of the present invention generally comprises a filter element 26 and securing means 28. FIG. 1 illustrates the present inventive apparatus. The filter 10 is placed onto the open end 16 of the tracheostomy tube 12 such that the securing means 28 engages the outer periphery 22 of the end cap 20. The securing means 28 is also attached to the filter element 34 and holds the filter onto the tracheostomy tube 12 and over the opening 24 of the open end 16.

The filter element 34 for the tracheostomy tube 12 has a filtering section 30 for filtering out airborne particles and contaminants from an air stream upon inhalation by an individual utilizing the tracheostomy tube 12. The filter element 34 is made up of two or more layers of net material 32. The two layers are aligned such that the mesh of one section of net material is offset from the net of the second net material. This type of alignment forms a micro porous membrane 34 in the filtering section 30 to filter out airborne contaminants. The net material in each layer may also be different mesh sizes.

Figure 4:
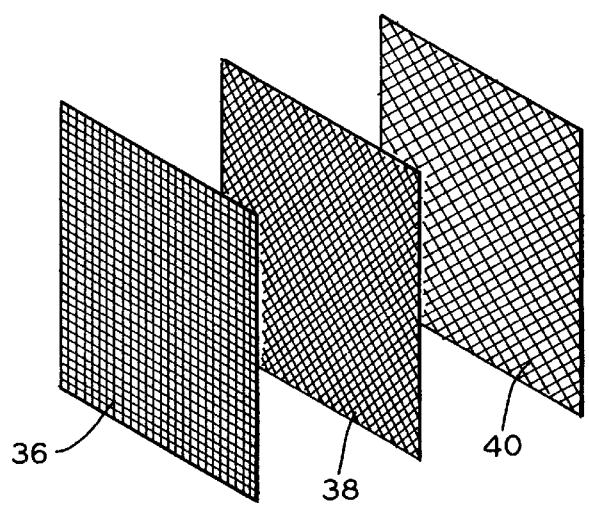
FIG. 4 is perspective view of the layers of net material prior to being combined to form the micro porous membrane.

Alternatively, the micro porous membrane 34 can be made up of a plurality of layers of net material, each layer having a different mesh size and being randomly aligned with respect to each other to improve the filtering capability of the present invention. FIG. 4 depicts three layers 36, 38, 40 of net material separated to indicate the various mesh sizes and the random positioning of the alignment of the net material to form the micro porous membrane 34. The net material may range in mesh sizes from a very fine mesh to a coarse mesh. In a preferred embodiment, a very fine layer of net material is placed between two coarse outer layers of net material.

In general, the filtering section 30 of the present invention separates airborne contaminants and particles from the inhaled air stream of a nominal 1 micron in diameter. The multi-layer filter element, which forms the micro porous membrane 34 in the filtering section, is capable of separating particles from about 1 to 10 microns.

An annular securing means 28 is utilized in the present invention to hold the filter 10 in place on the tracheostomy tube 12. The securing means 28 may involve various forms to engage the outer periphery 22 of the open end 16 of the tracheostomy tube 12. The securing means 28 also is connected to the filter element 26 so that as the securing means 28 engages the outer periphery 22 of the open end 16 the filter element 26 is pulled onto the open end 16 of the tracheostomy tube 12. In this alignment, the micro porous membrane 34 of the filtering section 30 is positioned directly over the opening 24 of the open end 16.

The securing means 28 of the present invention illustrated in FIG. 1 is a carbon steel or metal ring sewn between the layers of net material 32. The ring 42 is forced onto the open end 16 such that the net material 32 between the ring 42 and the outer periphery 22 causes the ring to frictionally engage the tracheostomy tube 12 and hold the filter 10 in place.

Alternatively, the ring may be made of resilient material, such as a synthetic rubber, that is stretched over the open end 16 of the tube 16 until appropriately positioned. The resilient ring returns to its unstretched position to engage the outer periphery 22 of the open end 16.

Figure 2:
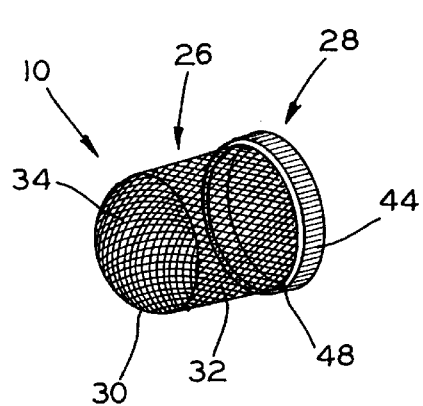
FIG. 2 is a perspective view of the apparatus of the present invention with an elastic securing means and a filtering section with a stiffened dome.

The elastic band 44 in FIG. 2 illustrates another means for securing the filter 10 onto the tracheostomy tube 12. The band 44 is sewn to an edge 48 of the filter element 26. The band is then stretched over the open end 16 of the tracheostomy tube 12 and placed accordingly onto the tube 12 so that the filtering section 30 covers the opening 24.

Figure 3:
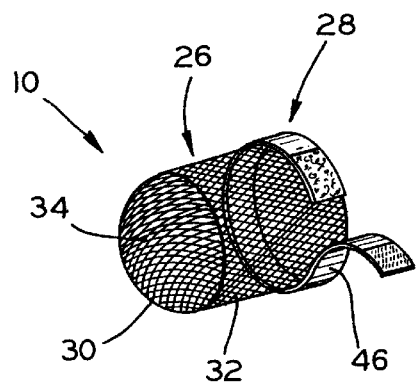
FIG. 3 is a perspective view of the apparatus of the present invention with a hook and mesh securing means and a filtering section with a stiffened dome.

An additional means for securing the filter 10 in place on the tracheostomy tube 12 is depicted in FIG. 3. The figure illustrates the use of a hook and mesh fastener 46 to which the filter element 26 is attached. The hook and mesh fastener strip 26 is then used to engage the tracheostomy tube 12 and hold the micro porous membrane 34 over the opening 24.

In an alternative embodiment, the micro porous membrane 34 of the filtering section 30 may be stiffened to form a dome-shaped filtering section, as indicated in FIGS. 1 to 3. A stiffening agent, such as starch or a polymer, is applied to the net material and then heat molded to form a rigid filtering section. The stiffened section assists in the filtration process by preventing the filtering section 30 from becoming overly wet from moisture and sputum discharged upon exhalation by the individual.

The net material utilized for the individual layers is generally a nylon fabric. However, other net material made from various natural or synthetic fibers is suitable for use with the present invention.

Having set forth a description of the structure of the present invention, the use and function of the tracheostomy tube filter may now be described with particular reference to FIGS. 1.

The filter 10 may be placed over the open end 16 of a tracheostomy tube 12 through the use of the securing means 24 as previously described. The device is positioned so that the micro porous membrane 34 of the filtering section 30 covers the opening 24 of the tracheostomy tube 12. Once in place, the micro porous membrane 34 allows air to pass through the membrane, upon inhalation by the individual, while separating out airborne particles and contaminants. The particles collect upon the outer exposed surface of the micro porous membrane 34.

The filter 10 may be left in place on the end of the tracheostomy tube 12 until air passage becomes restricted by the build up of filtered material. The filter 10 may then be simply removed and cleaned by either forcing air or water through the filter from the opposing side of the filtering section. Additionally, depending upon the form of the filtered material, the filter may be cleaned by simply wiping or manually removing the filtered contaminants from the micro porous membrane 34 of the filtering section 30.

The present invention is well suited for use in situations where an uncomplicated, low cost filter is needed. This is particularly true in emergency situation where a victim requires an emergency tracheostomy and is temporary confined in an unclean environment and cannot be quickly removed. The present invention provides suitable protection and prevents damaging particulate matter from entering the lungs. Additionally, the present invention may be utilized by any individual with a tracheostomy tube who desires an unobtrusive filtration device to prevent particulate matter from entering their lungs.

In accordance with the provisions of the patent statutes, the present invention has been described in what is considered to represent its preferred embodiment. However, it should be noted that the invention can be practiced otherwise than as specifically illustrated and described without departing from its spirit and scope.

What is claimed is:

1. A filter for a tracheostomy tube having an insertion end for insertion into an individual and a tubular open end, comprising:
   (a) a securing means for engaging an outer periphery of the open end of the tracheostomy tube while the insertion end of the tracheostomy tube is inserted into an individual; and
   (b) a filter element having two or more layers of net material forming a stiff, generally dome shaped filtering section, said layers being randomly aligned to create a micro porous membrane, said filter element being attached to said securing means so that as said securing means is placed over the tracheostomy tube the filtering section covers the open end, whereby said micro porous membrane separates airborne contaminants from an airstream upon inhalation by the individual through the tracheostomy tube.

2. A filter as recited in claim 1, wherein the filtering section of the filter element includes a stiffening agent applied to the net material.

3. A filter as recited in claim 2, wherein the stiffening agent is a polymer.

4. A filter as recited in claim 2, wherein the stiffening agent is a starch.

5. A filter as recited in claim 1, wherein the filtering section of the filter element includes an inner layer and two outer layers of net material, said inner layer being of smaller mesh size than the outer layers, each of said layers being stiff and generally dome shaped.

6. A filter as recited in claim 1, wherein said securing means comprises a securing ring for frictionally engaging an outer periphery of the open end of the tracheostomy tube.

\* \* \* \* \*